United States Patent [19]

Woodard et al.

[11] Patent Number: 5,342,931
[45] Date of Patent: Aug. 30, 1994

[54] PROCESS FOR PURIFYING DNA ON HYDRATED SILICA

[75] Inventors: Daniel L. Woodard, Raleigh; Adriann J. Howard, Durham; James A. Down, Cary, all of N.C.

[73] Assignee: Becton, Dickinson and Company, Franklin Lakes, N.J.

[21] Appl. No.: 51,596

[22] Filed: Apr. 23, 1993

Related U.S. Application Data

[63] Continuation of Ser. No. 835,179, Feb. 13, 1992, abandoned.

[51] Int. Cl.$^5$ .................. C12P 19/34; C12Q 1/68; C07H 21/00; C07H 21/04
[52] U.S. Cl. .................. 536/25.4; 435/6; 435/274; 935/19
[58] Field of Search .................. 536/25.4; 435/19, 6, 435/274, 91

[56] References Cited

U.S. PATENT DOCUMENTS

| | | | |
|---|---|---|---|
| 4,822,681 | 4/1989 | Schossler et al. | 428/405 |
| 4,833,234 | 5/1984 | DeBonville et al. | 536/27 |
| 4,900,677 | 2/1990 | Hewitt | 435/259 |
| 4,921,952 | 5/1990 | Longmire et al. | 536/27 |
| 4,923,978 | 5/1990 | McCormick | 536/27 |
| 5,075,430 | 12/1991 | Little | 536/27 |
| 5,106,966 | 4/1992 | Thomas et al. | 536/27 |
| 5,155,018 | 10/1992 | Gillespie et al. | 536/25.4 |
| 5,175,271 | 12/1992 | Thomas et al. | 536/25.4 |
| 5,234,809 | 8/1993 | Boom et al. | 536/25.4 |

FOREIGN PATENT DOCUMENTS

WO91/00924 1/1991 PCT Int'l Appl. .
2074892A 11/1981 United Kingdom .

OTHER PUBLICATIONS

R. Boom et al. J. Clin. Micro. 28(3):495-503, 1990.
M. A. Marko et al. Anal. Biochom. 121:382-387, 1982.
Erik H. Willis et al. Biotechniques 9(1):92-99, 1990.
Sek C. Chow et al., *Analytical Biochemistry* 183:42 (1989).
Randy M. McCormick *Analytical Biochemistry* 181:66 (1989).
Louise H. Lutze et al., *Nucleic Acids Research* 18:6150 (1990).
Bert Vogelstein et al., *Proc. Natl. Acad. Sci.* 76:615 (1979).

*Primary Examiner*—Johnnie R. Brown
*Assistant Examiner*—Gary L. Kunz
*Attorney, Agent, or Firm*—Donna R. Fugit

[57] ABSTRACT

A process for purifying DNA comprising 1) binding the DNA to a hydrated silica in the presence of water or physiological buffers in which the hydrated silica is prepared by refluxing silicon dioxide in sodium hydroxide or potassium hydroxide at a molar ratio of about 2:1 to 10:1 for at least about 48 hours, 2) separating and washing hydrated silica and the DNA bound thereto, and eluting the DNA from the hydrated silica in a heated physiological buffer or in heated water.

3 Claims, No Drawings

PROCESS FOR PURIFYING DNA ON HYDRATED SILICA

This application is a continuation of application Ser. No. 07/835,179, filed Feb. 13, 1992, abandoned.

FIELD OF THE INVENTION

The invention is in the field of molecular biology. In particular, the invention is in the area of deoxyribonucleic acid purification.

BACKGROUND OF THE INVENTION

The continued advances in molecular biology and related disciplines present continued needs for improvements in tools associated with fully appreciating and developing the advanced technology.

A wide range of technologies involve the use of deoxyribonucleic acids (DNA) in a variety of forms. For example, advances in the area of recombinant DNA technology continually require the use of DNA in the form of probes, genomic DNA, and plasmid DNA.

Advances in the area of diagnostics also continue to utilize DNA in a variety of ways. For example, DNA probes are routinely used in the detection and diagnosis of human pathogens. Likewise, DNA is used in the detection of genetic disorders. DNA is also used in the detection of food contaminants. And, DNA probes are routinely used in locating, identifying and isolating target DNA of interest for a variety of reasons ranging from genetic mapping to cloning and recombinant expression.

In many instances DNA is available in extremely small amounts, and isolation and purification procedures can be laborious and time consuming. The often time consuming and laborious procedures can lead to loss of DNA. In the purification of DNA from specimens obtained from serum, urine, and bacterial cultures, there is the added risk of contamination and false-positive results.

Typical DNA purification protocols involve the use of caustic and poisonous compositions. The typical DNA purification protocol uses high concentrations of chaotropic salts such as sodium iodine and sodium perchlorate.

There are numerous protocols for purifying DNA. As evidenced by recent activity in the area of DNA purification, there is a continued pursuit for optimal DNA purification protocols. U.S. Pat. No. 4,923,978 discloses a process for purifying DNA in which a solution of protein and DNA is passed over a hydroxylated support and the protein is bound and the DNA is eluted. U.S. Pat. No. 4,935,342 discloses purification of DNA by selective binding of DNA to anion exchangers and subsequent elution. U.S. Pat. No. 4,946,952 discloses DNA isolation by precipitation with water-soluble ketones. A DNA purification procedure using chaotropes and dialyzed DNA is disclosed in U.S. Pat. No. 4,900,677.

While the present protocols for purifying DNA are able to accomplish their goal, it is desirable to purify DNA without the use of such caustic and poisonous compounds such as the most often used chaotropes in addition to obtaining increased amounts of DNA.

SUMMARY OF THE INVENTION

The invention provides the monomer unit composition:

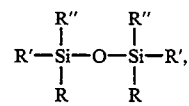

wherein R' is OH, R is SiO$_2$, and R" is OH and repeating units of the composition comprising the formula:

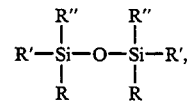

wherein R' is independently OH or

R is SiO$_2$, and R" is independently OH or

and compositions comprising the above monomer and repeating units thereof. Repeating units described above can include from about 2 up to infinity. Ranges include about 2 to about 100,000,000, and about 2 to about 100,000.

The invention can be used to purify DNA from a variety of sources and from a variety of forms. The process uses the composition of the invention and renders the use of binding buffers, such as chaotropes, optional. The DNA can be bound in aqueous solution such as TE buffer (10 mM Tris, 1 mM EDTA) at room temperature. In addition, the DNA can be eluted into water from the compositions of the invention by heating, or generally used elution buffers such as TE or 1 X TAE (Tris/acetate/EDTA) can be employed. Sources of DNA for purification include bacteria, bacteriophage, specimens, plants, animals, and the like. DNA can be found in a variety of forms and includes single-stranded, double-stranded, circular, and linear. The invention can be practiced with DNA from any source in any form.

DETAILED DESCRIPTION

The invention provides the monomer unit composition:

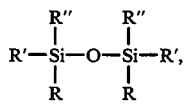

wherein R' is OH, R is SiO$_2$, and R" is OH and repeating units of the composition comprising the formula:

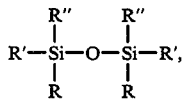

wherein R' is independently OH or

R is SiO$_2$, and R" is independently OH or

and compositions comprising the above monomer and repeating units thereof. Repeating units described above can include from about 2 up to infinity. Ranges include about 2 to 100,000,000, and about 2 to 100,000.

The surface provides for bonding of DNA while also allowing easy recovery of DNA from the surface.

Also provided is a process for purifying DNA which comprises contacting DNA with a composition of the formula:

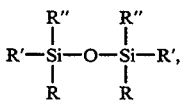

wherein R' is OH, R is SiO$_2$, and R" is OH or repeating units of the composition comprising the formula:

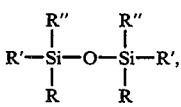

wherein R' is independently OH or

R is SiO$_2$, and R" is independently OH or

Reaction products of hydrating reagents and SiO$_2$ are also provided.

The invention also provides a method for making the composition of the formula:

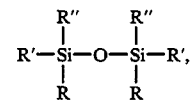

wherein R' is OH, R is SiO$_2$, and R" is

and repeating units of the composition comprising the formula:

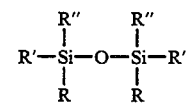

wherein R' is independently OH or

R is SiO$_2$, and R" is independently OH or

Repeating units described above can include from about 2 up to infinity. Ranges include about 2 to 100,000,000, and about 2 to 100,000.

Generally, reaction products of hydrating reagents and SiO$_2$ result in a bead like structure comprising repeating units of the above referenced monomer unit.

It is possible that the electronic nature of this polymer is such that surface modifications can be made that are of a more conventional nature but are changed electronically due to the presence of this polymer being at the center of the bead (making it a more efficient surface for the purposes described in this disclosure). For example, the surface could be modified with SiCl$_4$ followed by hydration which would result in a silanol coating on the surface. The exposure of the repeating unit is what interacts with the DNA, and thus surfaces comprising the repeating unit are also suitable for practicing the invention. Surfaces which can be designed to comprise compositions of the invention include dipstick configurations, tubes, vials, filtration devices, and the like.

The procedure for obtaining the compositions of the invention generally comprises adding a hydrating reagent like NaOH(aq) to SiO$_2$ and refluxing.

The invention also provides a process for purifying DNA which comprises contacting DNA with compositions of the invention.

The process for producing the compositions of the invention and the reaction products of NaOH and SiO$_2$ comprises the addition of NaOH to SiO$_2$. Any counter ion, not just Na$^+$, can be used in any concentration and in any ratio compared to SiO$_2$. For example, potassium hydroxide can also be used. The ratio of NaOH to SiO$_2$ is about 0.1:1–10:1, preferably about 2:1. The resultant product is filtered then washed and dried. Suitable washing reagents include acetone and the like. The product is now ready for use in purifying DNA.

The start of any DNA purification or isolation procedure requires obtaining the desired DNA from its source. Typical protocols for obtaining DNA from specimens such as serum, urine and bacterial cultures are well known and routinely carried out. Likewise, the ability to obtain DNA from genomic libraries and the like are routine. The key to the invention is the ability to purify DNA, once obtained from its source. Typical procedures for obtaining DNA end with a suspension of the DNA in solution. References include those for isolation of DNA from biological samples, Harding, J. D., Gebeyehu, G., Bebee, R., Simms, D., Ktevan, L., *Nucleic Acids Research*, 17:6947 (1989), and Marko, M. A., Chipperfield, R., and Birnboim, H. C., *Analytical Biochemistry*, 121:382 (1982). Procedures for isolation of plasmid DNA can be found in Lutze, L. H., Winegar, R. A., *Nucleic Acids Research* 20:6150 (1990). Extraction of double-stranded DNA from biological samples can be found in Yamada, O., Matsumoto, T., Nakashima, M., Hagri, S., Kamahora, T., Ueyama, H., Kishi, Y., Uemura H., Kurimura, T., *Journal of Virological Methods* 27:203 (1990). Most DNA solutions comprise the DNA in a suitable buffer such as TE (Tris-EDTA (10 mM:1 mM)), TEA (40 mm Tris-acetate, 1 mm EDTA) buffer, or a lysate.

Once the DNA is obtained in a suitable solution, a binding matrix is typically added to the solution. Generally used binding matrixes are silica in the form of glass or diatoms. However, procedures using silica require high concentrations of chaotropes or alcohols for the DNA to bind to the surfaces. Currently used chaotropes include sodium iodide (NaI), urea, guanidinium Hydrochloride, sodium perchlorate (NaClO$_4$), and potassium bromide (KBr). Chaotropes and alcohols can be toxic, caustic, flamable and/or expensive. The process of the present invention does not require the presence of chaotropes or alcohols for binding to surfaces of the invention. Processes of the invention bind DNA in an aqueous solution at room temperature and elute the DNA in water at 37° C. However, if desired, chaotropes, alcohols and the like can be used with the process of the invention.

Typical procedures for using the process of the invention include the addition of the composition of the invention to a solution of DNA, which is generally followed by the addition of a binding buffer. At this point, it is advantageous that the process of the invention does not require a binding buffer. The solution can be incubated for a brief period at room temperature. After spinning, the supernatant can be discarded and the pellet washed. The DNA can then be eluted.

The composition of the invention is typically used in weight ranges from about 1:10 to 1:1 composition weight:water. Preferably excess amounts of water are avoided and buffers such as TE can be used in place of water.

Next, a binding buffer is added, if used. After a brief incubation period at room temperature from about 1 to 20 minutes, preferably about 10, the container can be spun to obtain a pellet and supernatant fractions. The supernatant is separated and the pellet is washed with a reagent such as ethanol diluted with 50 mM Tris. A preferred wash reagent concentration is 80% ethanol. DNA can then be eluted from the compositions of the invention by using elution buffers such as TE buffer, 1 X TAE buffer, and 1 X TBE (Tris/borate/EDTA) buffer. More importantly, the use of elution buffers can be eliminated altogether, and DNA eluted in water by heating. For maximum yields the elution step can be repeated.

The chemical compositions of the invention can be conveniently assembled into a kit. A kit comprising the composition of the invention can include the composition in a container, such as a vial, with a suitable buffer, such as TE buffer and TAE buffer and optionally include a container of a binding buffer such as chaotropes, a container of wash buffer, such as a solution of ethanol diluted with 50 mM tris or 1 X TAE, and a container of elution buffer, such as TE buffer, 1 X TAE buffer, and 1 X TBE buffer. Such a kit would allow convenient purification of DNA.

The following examples illustrate the specific embodiments of the invention described in this document. As would be apparent to skilled artisans, various changes and modifications are possible and are contemplated within the scope of the invention described.

EXAMPLES

Example 1

The purpose of this experiment is to increase the surface hydroxyl groups on celite 545, acid washed, by refluxing in various solutions of NaOH. The increased presence of hydroxyls allows for easier modifications of the surface by chemical reactions.

Materials

Celite 545, acid washed (Alltech, Deerfield, Ill, stock #9043, QC 243)

NaOH (Aldrich Lot #04027EP)

Eight experiments were set up exactly the same way except that the amount of NaOH was varied from one experiment to the next.

| Experiment | Celite 545 | | NaOH | | eq celite |
|---|---|---|---|---|---|
| | g | mMol | mg | mMol | |
| 1 | .5 | 8.33 | 16.8 | .42 | .05 |
| 2 | .5 | 8.33 | 33.2 | .83 | .1 |
| 3 | .5 | 8.33 | 100.0 | 2.50 | .3 |
| 4 | .5 | 8.33 | 168.0 | 4.20 | .5 |
| 5 | .5 | 8.33 | 233.0 | 5.83 | .7 |
| 6 | .5 | 8.33 | 333.0 | 8.33 | 1 |
| 7 | .5 | 8.33 | 500.0 | 12.50 | 1.5 |

| Experiment | Celite 545 g | mMol | NaOH mg | mMol | eq celite |
|---|---|---|---|---|---|
| 8 | .5 | 8.33 | 666.0 | 16.66 | 2 |

In a typical experiment, the celite 545 is added to a round bottom flask followed by the NaOH dissolved in 10 ml $H_2O$. Reflux 48 hours with stirring. Filter, wash with water and acetone and air dry. Store in a desicator.

Results and Conclusions for Example 1:

FTIR analysis was done showing increase in the —OH signal of hydrated surfaces compared to the starting material.

Example 2

This experiment describes how the DNA binding capacity of SUPER FINE SUPER FLOSS CELITE (Manville) was determined and how that compares to the Prep-A-Gene DNA purification kit.

Materials

Super Fine Super Floss (SFSF) (Sample from Manville,

Denver, Co. (1:5 w/w in $H_2O$))

λDNA (BRL Cat. 56125A, Lot AJU702)

50 mM Tris pH7.0 (Dilute from 1M stock) BRL Cat. 5505UA, Lot

60926

(PREP-A-GENE KIT (Bio-Rad, Richmond, Calif.))

Binding Buffers (Diluted from 6M stock) $NaClO_4$ Fisher

Cat. 5490-500, Lot 914199

Wash Buffer 80% Ethanol in 50 mM Tris, pH7.0

Elution Buffer Milli Q $H_2O$

Ethidium Bromide (10 mg/ml) Sigma Cat. E-8751, Lot 99F3722

1% agarose BRL Cat. 5510UA, Lot 9N2204

1 X TAE (from 50 X stock) Tris Base-Sigma CAT T-1503, Lot

80H5633 Acetic Acid—Fisher A38-500 EDTA—Sigma CAT

ED255, Lot 117F-0026

Type II Loading Dye (25% Ficoll 400, 0.25% Bromophenol Blue, 0.25% xylene cyanol Ficoll 400—Sigma CAT F4375, Bromophenol Blue—BIO-RAD CAT 161-0404, Lot M 1264, Xylene Cyanole—Sigma CAT X-4126, Lot 8043740)

Type 57 and 55 POLAROID Film

Methods

1. Two groups of reactions are set up, one for each surface type. Each surface has 8 tubes containing 50 μl of the DNA solution. This solution is 0.5 μl λDNA in 50 μl 50 mM Tris, pH7.0 for 31 μg DNA/reaction. The titration ranges from 0M $NaClO_4$ to 6M $NaClO_4$.
2. Add 20 μl of each surface to the reaction mixes.
3. Add 400 μl Binding Buffer according to the titration. For Prep-A-Gene this was 0M, 2M, 2.5M, 3M, 3.5M, 4M, 4.5M, and 6M $NaClO_4$. For SFSF, the titration is 0M, 1M, 1.5M, 2M, 2.5M, 3M, 3.5M, and 4M $NaClO_4$.
4. Incubate for 10 minutes, with rocking, at room temperature.
5. Spin and discard supernatant.
6. Wash pellet 2 times with 80% ethanol/50 mM Tris, pH7.0.
7. Elute DNA in 20 μl $H_2O$, 37° C., 10 minutes.
8. Spin and remove supernatant to a separate tube. Repeat elution step and combine supernatants for ~40 μl total.
9. Add 2 μl, Type II loading dye to each tube.
10. Load onto a 1% agarose, 1 X TAE gel. Run for ~25 minutes at 100–130 volts in 1 X TAE buffer.
11. Stain with ethidium bromide in $H_2O$ (~1:1000) for ~15 minutes. Destain for ~20–30 minutes.
12. Photograph over UV light with Type 57 Polaroid film. If possible, take negatives with Type 55 film.

Results and Conclusions

SFSF celite binds DNA strongly at a binding buffer concentration of 2.5 m $NaClO_4$ compared to Prep-a-Gene's matrix which requires 3M $NaCl_4$ for binding DNA. For this reason SFSF will be used as the standard for comparison to the hydrated surfaces.

Example 3

The purpose of the following experiment is to determine at what concentration of binding buffer will the hydrated $SiO_2$ surfaces allow recovery of DNA from a sample. The results will be compared to Super Fine Super Floss celite.

Surfaces
1. Acid washed Celite 545+0.05 eq NaOH.
2. Acid washed Celite 545+0.1 eq NaOH.
3. Acid washed Celite 545+0.3 eq NaOH.
4. Acid washed Celite 545+0.5 eq NaOH.
5. Acid washed Celite 545+0.7 eq NaOH.
6. Acid washed Celite 545+1 eq NaOH.
7. Acid washed Celite 545+1.5 eq NaOH.
8. Acid washed Celite 545+2.0 eq NaOH.
9. Super Fine Super Floss celite.

The remainder of materials and methods are set forth and carried out in substantial accordance with the teachings of Example 2.

| Celite + NaOH | Results: Concentration of Binding Buffer Required for Strong DNA Binding to the Test Surface DNA Binding 1M–4M [$NaClO_4$] |
|---|---|
| .05 eq NaOH | + |
| .10 eq NaOH | + |
| .30 eq NaOH | ++ 1.5M |
| .50 eq NaOH | ++ 2.0M |
| .70 eq NaOH | ++ 2.0M |
| 1.0 eq NaOH | ++ 2.0M |
| 1.5 eq NaOH | ++ 1.5M |
| 2.0 eq NaOH | +++* |
| SFSF celite | ++ 3.0M |

+ Trace amounts of DNA elute across the titration
++ Near complete elution of DNA from 1.5, 2.0 or 3.0M $NaClO_4$.
+++ Near complete elution of DNA across the titration.
*Eluted DNA under native conditions. DNA binds in water at room temperature and eluted at 37° C. in water.

Conclusion

The results of gel electrophoresis demonstrates that as the amount of NaOH was increased in proportion to celite, the recovery of DNA from the resulting surface increased as well. As The mole ratio of NaOH:celite reaches 2.0, DNA was recovered under native conditions (no binding buffer required). Most of the surfaces isolated the DNA better than SFSF celite, without requiring concentrated amounts of binding buffer generally required to bring this about.

Although the invention has been described with respect to specific modifications, the details thereof are not to be construed as limitations, for it will be apparent that various equivalents, changes and modifications may be resorted to without departing from the spirit and scope thereof, and it is understood that such equivalent embodiments are to be included therein.

What is claimed is:

1. A process for purifying DNA which comprises:
   a) binding the DNA to a hydrated silica compound in the presence of water or physiological buffers, wherein the hydrated silica compound is produced by the process of refluxing a mixture of $SiO_2$ and sodium hydroxide or potassium hydroxide at a molar ratio of about 2:1 to 10:1 for at least about 48 hours;
   b) separating and washing the hydrated silica compound and the DNA bound thereto; and
   c) eluting the DNA from the hydrated silica compound in a heated physiological buffer or in heated water.

2. The process of claim 1 wherein the DNA is bound to the hydrated silica in the solution selected from the group consisting of water, TRIS/EDTA buffer, TRIS/acetate/EDTA buffer, and TRIS/borate/EDTA buffer.

3. The process of claim 1 wherein the DNA is eluted by heated water.

* * * * *